United States Patent [19]

Kobayashi et al.

[11] Patent Number: 5,047,564
[45] Date of Patent: Sep. 10, 1991

[54] FLUORINE-CONTAINING VITAMIN $D_2$ DERIVATIVES

[75] Inventors: Yoshiro Kobayashi, Tokyo; Takeo Taguchi, Hachioji; Nobuo Ikekawa, Musashino, all of Japan

[73] Assignee: Taisho Pharmaceutical Co., Ltd., Japan

[21] Appl. No.: 151,931

[22] Filed: Feb. 3, 1988

[30] Foreign Application Priority Data

Feb. 10, 1987 [JP] Japan ............................ 62-29423

[51] Int. Cl.$^5$ .............................................. C07J 9/00
[52] U.S. Cl. ................................................. 552/653
[58] Field of Search ................. 514/167; 260/397.2; 552/653

[56] References Cited

U.S. PATENT DOCUMENTS

| | | | |
|---|---|---|---|
| 4,248,791 | 2/1981 | DeLuca et al. | 260/397 |
| 4,284,577 | 8/1981 | Yamada et al. | 260/397.2 |
| 4,521,410 | 6/1985 | Holick et al. | 260/397.2 |
| 4,613,594 | 9/1986 | Baggiolini et al. | 514/167 |

FOREIGN PATENT DOCUMENTS 0182298 11/1985 European Pat. Off. .

OTHER PUBLICATIONS

Goodman et al., The Pharmacological Basis of Therapeutics, 1980, pp. 1544-1545.
"Induction of Monocytic Differentiation of HL-60 Cells by 1,25-Dihydroxyvitamin D Analogs", The Journal of Biological Chemistry, vol. 262, No. 25, 10-1-5-1987.

Primary Examiner—Frederick E. Waddell
Assistant Examiner—T. Criares
Attorney, Agent, or Firm—Lorusso & Loud

[57] ABSTRACT

A fluorine-containing vitamin $D_2$ derivative represented by the following formula

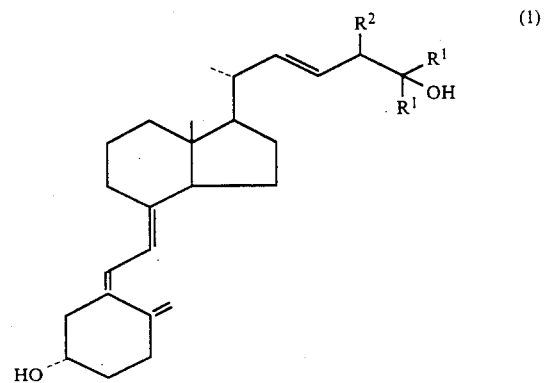

wherein $R^1$ represents a methyl or trifluoromethyl group, and $R^2$ represents a trifluoromethyl group when $R^1$ is a methyl group, and a hydrogen atom or a methyl group when $R^1$ is a trifluoromethyl group. This compound is useful for the prevention or treatment of calcium pathobolism or osteoporosis.

1 Claim, No Drawings

FLUORINE-CONTAINING VITAMIN $D_2$ DERIVATIVES

This invention relates to biologically active fluorine-containing vitamin $D_2$ derivatives. More specifically, it relates to vitamin $D_2$ derivatives having a fluorine-containing substituent, a process for production thereof and use thereof as pharmaceuticals.

Active-type vitamin D is useful for prevention and remedy of renal insufficiency, hypoparathyroidism, and bone diseases such as osteoporosis. In recent years, there has been an increasing interest in the possible utility of vitamin D homologs as an anticancer agent, a differentiation inducer for cancer, an immunomodulating agent, an antirheumatic agent and an antipsoriatic agent, and much research work has been undertaken on their synthesis.

Vitamin D and vitamin D derivatives have the activity of promoting calcium metabolism in bones, such as a bone-forming action (calcium deposition on bones) and a bone mineral dissolving action (liberation of calcium from bones) and the activity of increasing the serum calcium concentration. Because of these activities, they have been used for the prevention and treatment of osteoporosis and rickets. It is known however that the serum calcium elevating action of vitamin D derivatives by dissolving bone minerals and increasing the calcium absorption from the intestinal tract contributes to their pharmacological actions on the above diseases but at the same time cause deposition of calcium on tissues such as blood vessels, kidneys and digestive tracts and induce serious clinical side-effects such as arteriosclerosis and renal disorders.

Any strong vitamin D derivatives so far developed can be used only in limited amounts in clinical applications because of their activity of increasing the serum calcium concentration. Accordingly, their inherent antiosteoporotic effect, anticancer effect based on induction of differentiation, immunological effect and antipsoriatic effect cannot be fully exhibited.

Vitamin D derivatives which offer a solution to the above problem would be those which in spite of their weak actions associated with the increase of the calcium level in the blood such as an action of liberating calcium from bones, show a strong antiosteoporotic effect, anticancer effect, immunological effect and antipsoriatic effect. As a result of extensive efforts, we have now succeeded in developing novel fluorine-containing vitamin $D_2$ derivatives having such activities.

According to this invention there are provided fluorine-containing vitamin $D_2$ derivatives represented by the following formula

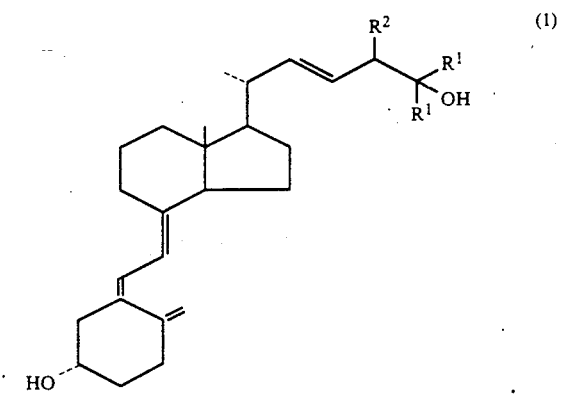

wherein $R^1$ represents a methyl or trifluoromethyl group, and $R^2$ represents a trifluoromethyl group when $R^1$ is a methyl group, and a hydrogen atom or methyl group when $R^1$ is a trifluoromethyl group.

The actions of the compounds of formula (1) provided by this invention which are associated with side-effects such as calcium liberation from bones are weak, and their vitamin D-like actions such as an anti-osteoporotic action and an antirickets action are strong. Accordingly, they are very useful as drugs for prevention and treatment of these diseases.

The compounds of formula (1) provided by this invention may be produced, for example, by any of the following processes A to C. The abbreviations used in the following reaction schemes have the meanings indicated below.

Et: ethyl
LCIA: lithium cyclohexyl isopropylamide
MOM: methoxymethyl
Ph: phenyl
mCPBA: m-chloroperbenzoic acid
LDA: lithium diisopropylamine
THP: tetrahydropyranyl
Ac: acetyl
p-TsOH: p-toluenesulfonic acid
DIBAL-H: diisobutyl aluminum hydride Reaction Scheme A

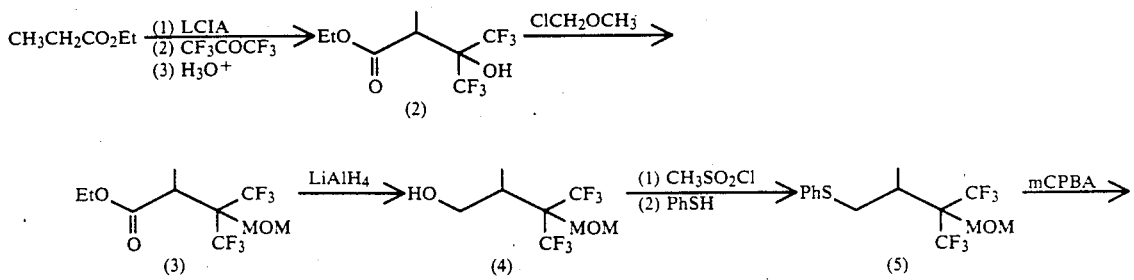

-continued
Reaction Scheme A
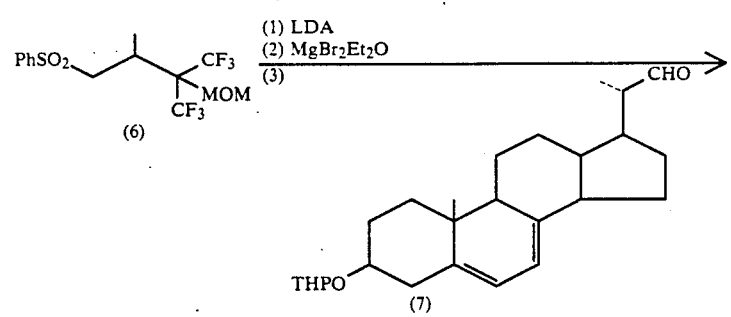
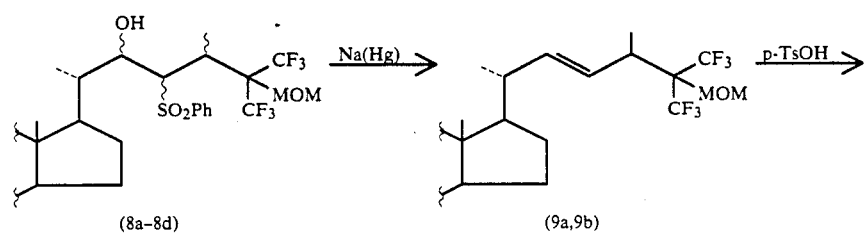
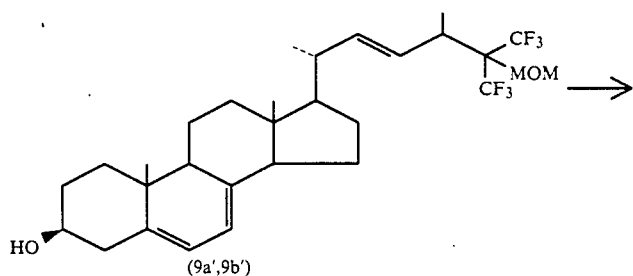
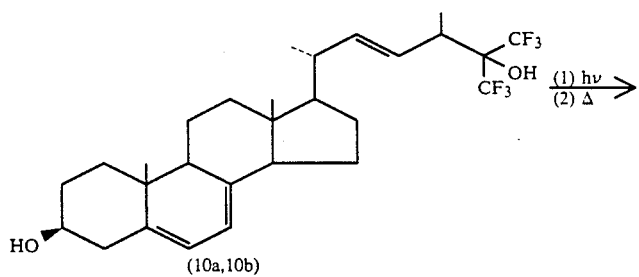
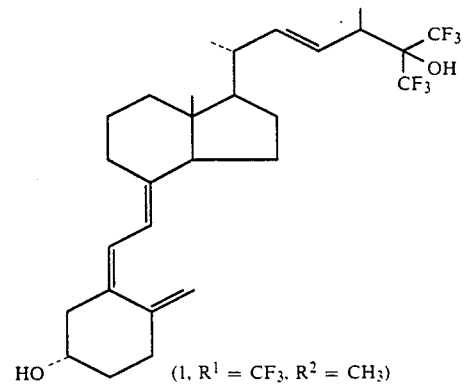

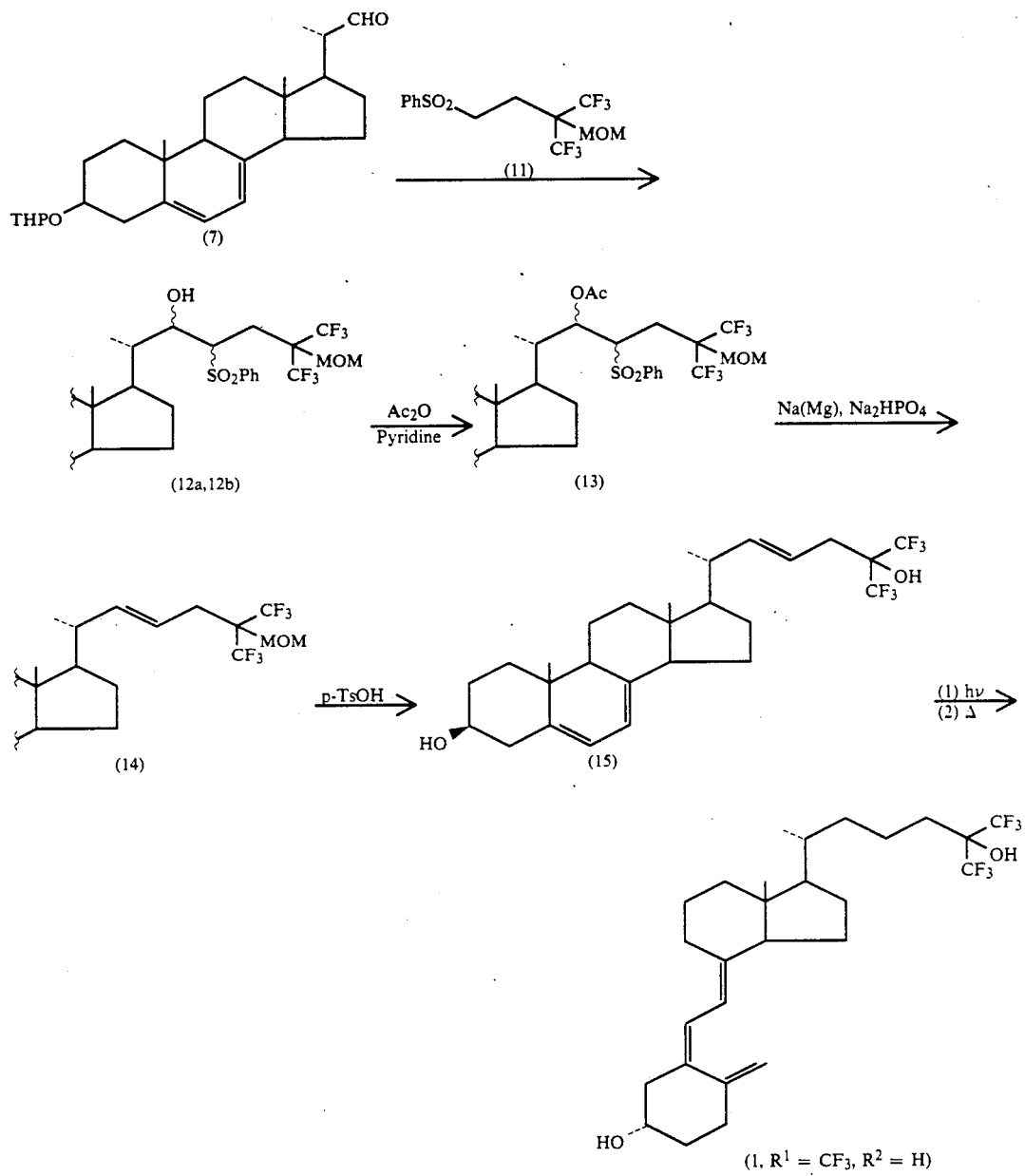
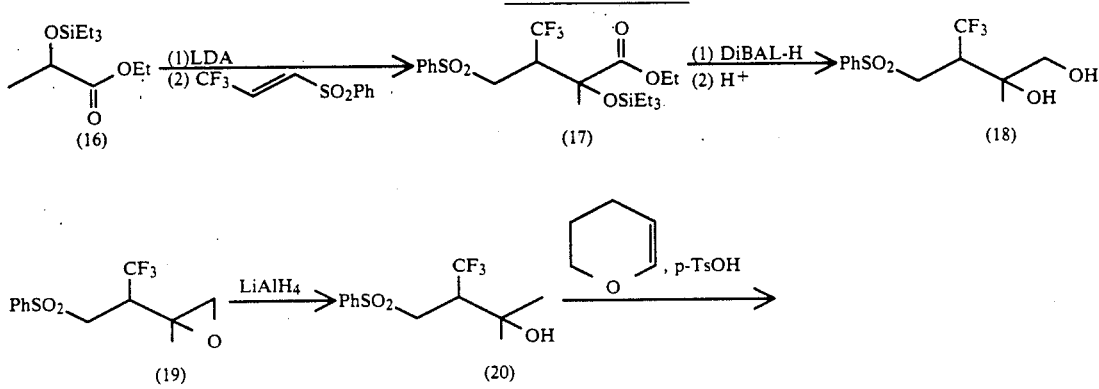

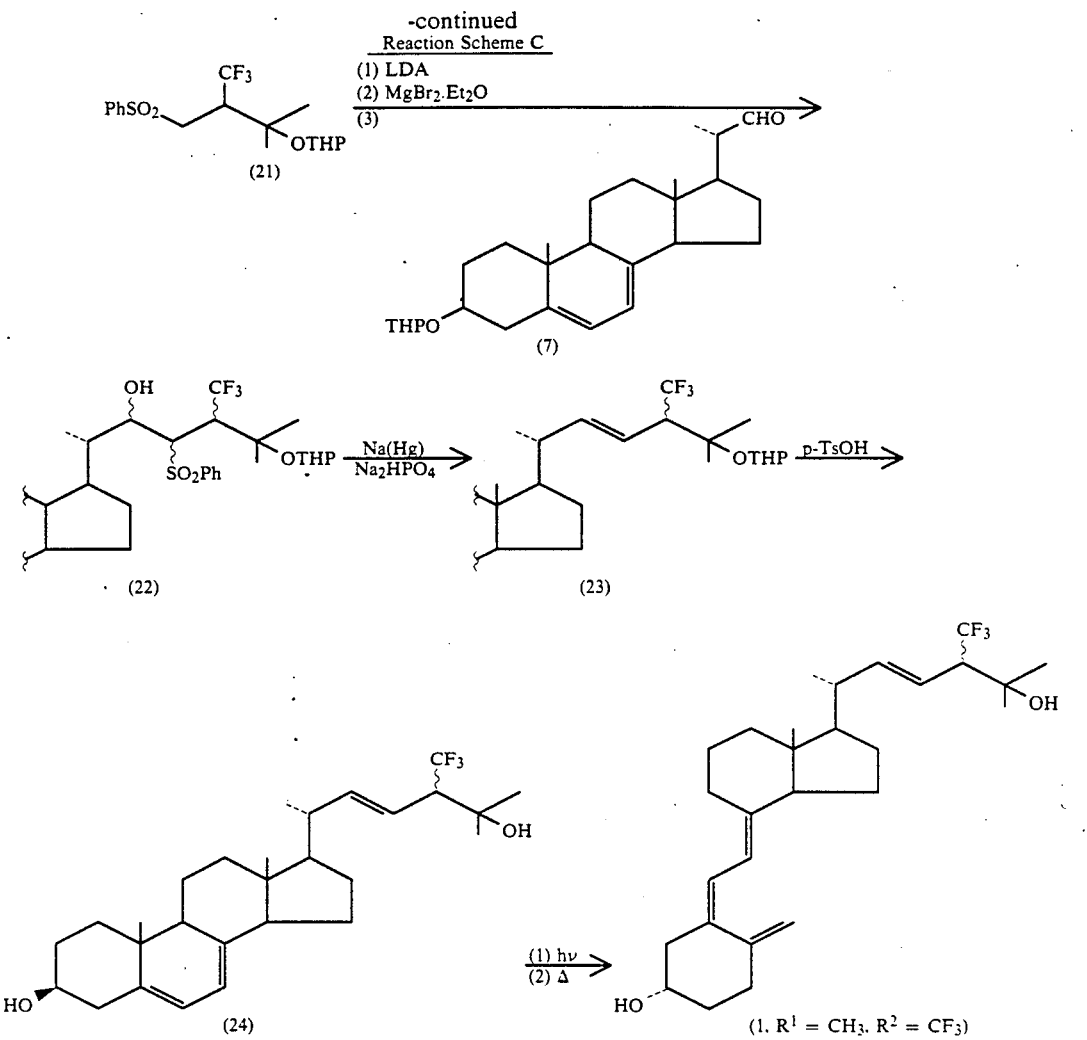

The following Examples more specifically illustrate the reaction conditions and other particulars in the individual steps of processes shown by the above reaction schemes A to C.

EXAMPLE 1

Production of 26,26,26,27,27,27-hexafluoro-25-hydroxyvitamin $D_2$ [$R^1$=$CF_3$, $R_2$=$CH_3$ in formula (1)] by reaction scheme A (a) Production of 3-hydroxy-2-methyl-3-trifluoromethyl-4,4,4-trifluorobutyric acid ethyl ester (2):

In a flask under an argon atmosphere, 26.9 ml (40 mmoles) of n-butyllithium (1.26M hexane solution) was added to a solution of 7.24 ml (44 mmoles) of N-isopropylcyclohexylamine in 50 ml of tetrahydrofuran at −78° C. (over a dry ice-acetone bath), and the mixture was stirred for 15 minutes. Then, 4.58 ml (40 mmoles) of ethyl propionate was added dropwise, and the mixture was stirred for 1 hour. A cold finger was attached to the flask, and 6.6 ml of hexafluoroacetone gas was introduced into the flask at −78° C. The mixture was stirred for 45 minutes. The excess of hexafluoroacetone was removed under reduced pressure, and the reaction mixture was poured into 1N hydrochloric acid and extracted with ether. The ether extract was washed with aqueous sodium chloride solution, and dried over anhydrous magnesium sulfate. The solvent was evaporated under atmospheric pressure. The residue was distilled under reduced pressure to give 9.66 g of the captioned compound (2) as a colorless oil.

b.p. 61°-100° C./71 mmHg
$^1$H-NMR (CDCl$_3$) δ:
1.32(3H, t, J=7Hz), 1.44(3H, d, J=7Hz),
3.08(1H, q, J=7Hz), 4.28(2H, d, J=7Hz),
5.42(1H, s).

(b) Production of 3-methoxymethoxy-2-methyl-3-trifluoromethyl-4,4,4-trifluorobutyric acid ethyl ester (3):

Under an argon atmosphere, 9.62 g of the compound (2), 10 mg of 4-dimethylaminopyridine, 26.13 ml (150 mmoles) of N,N-diisopropylethylamine and a solution of 9.11 ml (120 mmoles) of chloromethyl methyl ether in 40 ml of 1,4-dioxane were stirred at room temperature for 45 hours. The reaction mixture was poured into ice-dilute hydrochloric acid, and extracted with ether. The ether extract was washed with aqueous sodium chloride solution, saturated aqueous sodium bicarbonate solution and aqueous sodium chloride solution in this order, and dried over anhydrous magnesium sulfate. The solvent was evaporated under reduced pressure. The residue was distilled under reduced pressure to give 7.70 g of the captioned compound (3) as a colorless oil.

b.p. 67°-105° C./24 mmHg
$^1$H-NMR (CDCl$_3$) δ:
1.28(3H, t, J=7Hz), 1.43(3H, d, J=7Hz), 3.30(1H, q, J=7Hz), 3.53(3H, s),
4.22(2H, q, J=7Hz), 5.09,
5.14(2H, dx2, $J_{gem}$=7Hz).

(c) Production of 3-methyl-1,1,1-trifluoro-2-trifluoromethylbutane-2,4-diol 2-methoxymethyl ether (4):

Under an argon atmosphere, a solution of 7.63 g (24.4 mmoles) of the compound (3) in 20 ml of ether was added under ice cooling to a suspension of 930 mg (24.5 mmoles) of lithium aluminum hydride in 20 ml of ether, and the mixture was stirred for 1 hour. Water and then 10% hydrochloric acid were added to the reaction mixture, and the mixture was extracted with ether. The ether extract was washed with saturated aqueous sodium bicarbonate solution and then with aqueous sodium chloride solution, and dried over anhydrous magnesium sulfate. The solvent was evaporated under reduced pressure to give 6.06 g of the captioned compound (4) as a colorless oil.

b.p. 78°-109° C./27 mmHg
$^1$H-NMR (CDCl$_3$) δ:
1.27(3H, t, J=7.1Hz), 1.81(1H, t, J=5.5Hz),
2.47(1H, m), 3.50(3H, s), 3.53(1H, m),
4.01(1H, m), 4.93, 5.03(2H, dx2, $J_{gem}$=6.6Hz).

(d) Production of 3-methyl-4-phenylthio-1,1,1-trifluoro-2-trifluoromethylbutane-2-ol 2-methoxymethyl ether (5):

Under an argon atmosphere, 2.59 ml (33.46 mmoles) of methanesulfonyl chloride was added under ice cooling to a solution of 6.03 g (23.3 mmoles) of the compound (4) and 6.22 ml (44.63 mmoles) of triethylamine in 45 ml of methylene chloride, and the mixture was stirred at room temperature for 45 hours. The reaction mixture was poured into ice-dilute hydrochloric acid, and extracted with ether. The ether extract was washed with aqueous sodium chloride solution, dried over anhydrous magnesium sulfate, and concentrated under reduced pressure to give a mesylated product of the compound (4).

Then, under an argon atmosphere, 2.55 ml (24.83 mmoles) of thiophenol was added to a solution of 1.48 g (26.38 mmoles) of potassium hydroxide in 10 ml of ethanol and 10 ml of water, and the mixture was stirred for 20 minutes. Under ice cooling, a solution of the mesylated product in 10 ml of ethanol and 10 ml of water was added. The mixture was stirred at 60° C. for 24 hours. Water was added to the reaction mixture, and it was extracted with ether. The ether extract was washed with aqueous sodium chloride solution, dried over anhydrous magnesium sulfate, and concentrated under reduced pressure. The residue was purified by silica gel column chromatography (200 g; n-hexane:benzene=10:1) to give 3.57 g of the captioned compound (5).

$^1$H-NMR (CDCl$_3$) δ:
1.35(3H, d, J=7.0Hz), 2.45(1H, m),
2.68(1H, m), 3.42(3H, s),
3.49(1H, d, J=12.2Hz), 4.79,
4.81(2H, dx2, $J_{gem}$=6.4Hz), 7.21-7.43(5H, m).
$^{19}$F-NMR (CDCl$_3$) δ: −5.30(m), −5.87(m).

(e) Production of 3-methyl-4-phenylsulfonyl-1,1,1-trifluoro-2-trifluoromethylbutane-2-ol 2-methoxymethyl ether (6):

Under an argon atmosphere, 5.3 g (30.1 mmoles) of m-chloroperbenzoic acid (purity 70%) was added under ice cooling to a solution of 3.46 g (7.56 mmoles) of the compound (5) in 50 ml of methylene chloride, and the mixture was stirred for 13 hours. The precipitate was separated by filtration. A 1N aqueous solution of sodium hydroxide was added to the filtrate, and the mixture was extracted with methylene chloride. The methylene chloride extract was washed with a 1N aqueous solution of sodium hydroxide, dried over anhydrous magnesium sulfate and concentrated under reduced pressure. The residue was purified by silica gel column chromatography (200 g; n-hexane:ethyl acetate=8:1) to give 2.42 g of the captioned compound (6).

IR$\nu_{max}^{CHCl_3}$cm$^{-1}$:
3015, 2940, 1315, 1285, 1210, 1160, 1080.
$^1$H-NMR (CDCl$_3$) δ: 1.44(3H, d, J=6.5Hz), 3.04(1H, m), 3.09(1H, m), 3.42(3H, s), 3.62(1H, d, J=13.7Hz), 4.90, 4.94(2H, dx2, $J_{gem}$=6.2Hz), 7.58-7.95(5H, m).
$^{19}$F-NMR (CDCl$_3$) δ: −5.77(s).
MS m/e: 394(M+), 363(M+−CH$_3$O), 334, 314, 253(M+-phenylsulfonyl).
High resolution MS: for C$_{13}$H$_{13}$F$_6$O$_3$S(M+-13 CH$_3$O): Calculated: 363.0489; Found: 363.0489

(f) Production of 26,26,26,27,27,27-hexafluoro-23-phenylsulfonylergosta-5,7-diene-3β,22,25-triol -25-methoxy-methyl 3β-tetrahydropyranyl diether (8a-8b):

Under an argon atmosphere, n-butyllithium (1.45M hexane solution; 0.75 ml; 1.08 mmoles) was added to a solution of 152 microliters (1.08 mmoles) of diisopropylamine in 3 ml of tetrahydofuran at −78° C. (over a dry ice-acetone bath), and the mixture was stirred for 15 minutes. Then, a solution of 430 mg (1.09 mmoles) of the compound (6) in 4 ml of tetrahydrofuran was added, and under ice cooling, the mixture was stirred for 30 minutes. The reaction mixture was cooled to −78° C., a magnesium bromide-ether complex prepared from 207 microliters (1.09 mmoles) of 1,2-dibromoethane and 62 mg (2.55 mmoles) of metallic magnesium in 5 ml of ether was added. Furthermore, a solution of 297 mg (0.721 mmoles) of 22,23-bisnor-3β-tetrahydropyranyloxychol-5,7-dien-22-al (7) in 3 ml of tetrahydrofuran was added. The mixture was stirred for 1 hour, and extracted in a customary manner. The extract was purified by silica gel column chromatography (90 g; n-hexane:ethyl acetate=7:1-5:1 v/v) to give isomers of the captioned compound, (8a) (138 mg), (8b) (165 mg), (8c) (155 mg) and (8d) (20 mg) in the sequence of elution.

Isomer (8a) (amorphous compound)
IR$\nu_{max}^{KBr}$cm$^{-1}$: 3550, 2950, 1215, 1145, 1025, 725.
$^1$H-NMR (CDCl$_3$) δ: 0.47(3H, s), 0.57(3H, d, J=5Hz), 0.93(3H, s), 3.09(1H, d, J=8Hz), 3.50(3H, s), 4.25(1H, m), 4.74(1H, m), 5.10(2H, s), 5.40(1H, m), 5.57(1H, m), 7.45-8.03(5H, m).
$^{19}$F-NMR (CDCl$_3$) δ: −2.77(q, J=11Hz), −5.27(q, J=11Hz).
MS m/e: 722(M+-pyranyl), 704(M+-pyranyl, H$_2$O), 678, 660, 645.

Isomer (8b) (amorphous compound)
IR$\nu_{max}^{KBr}$cm$^{-1}$: 3530, 2950, 1215, 1150, 1060, 1025, 725. $^1$H-NMR (CDCl$_3$) δ: 0.42(3H, s), 0.71(3H, d, J=5Hz), 0.90(3H, s), 3.11(1H, d, J=5Hz), 3.50(3H, s), 4.79(1H, m), 5.16(2H, s), 5.39(1H, m), 5.60(1H, m), 7.56-8.13(5H, m).
$^{19}$F-NMR (CDCl$_3$) δ: −3.49(q, J=9Hz), −6.02(q, J=9Hz).
MS m/e: 806(M+), 766, 748, 722(M+-pyranyl), 704(M+-pyranyl, H$_2$O), 689, 678, 660, 650.

Isomer (8c) (amorphous compound)
IR$\nu_{max}^{KBr}$cm$^{-1}$: 3550, 2950, 1220, 1145, 1075, 1025, 730.

$^1$H-NMR (CDCl$_3$) δ: 0.63(3H, s), 0.94(3H, s), 1.15(3H, d, J=6Hz), 3.17(1H, m), 3.38 (3H, s), 4.40(1H, d, J=10Hz), 4.77(1H, m), 4.85, 4.94(2H, dx2, J$_{gem}$=5Hz), 5.41(1H, m), 5.56(1H, m), 7.47-8.09(5H, m).

$^{19}$F-NMR (CDCl$_3$) δ: −2.47(q, J=11Hz), −4.83(q, J=11Hz).

MS m/e: 806(M+), 766, 748, 722(M+-pyranyl), 660, 642, 627.

Isomer (8d) (amorphous compound)

IRν$_{max}$$^{KBr}$ cm$^{-1}$: 3510, 2950, 1275, 1210, 1135, 1075, 1030, 730. $^1$H-NMR (CDCl$_3$) δ: 0.59(3H, s), 0.67(3H, d, J=5Hz), 0.93(3H, s), 3.21(1H, d, J=4Hz), 3.49(3H, s), 4.20(1H, d, J=9Hz), 4.78(1H, m), 5.16(2H, s), 5.43(1H, m), 5.59(1H, m), 7.50-8.07(5H, m).

$^{19}$F-NMR (CDCl$_3$) δ: −2.50(q, J=10Hz), −6.90(q, J=10Hz).

MS m/e: 806(M+), 766, 748, 722(M+-pyranyl), 704(M+-pyranyl, H$_2$O), 689, 660, 642, 627.

(g) Production of 26,26,26,27,27,27-hexafluoro-ergosta-5,7,22(E)-triene-3β,25-dio- 25-methoxymethyl 3β-tetrahydropyranyl diether (9a, 9b):

Under an argon atmosphere, 3% sodium amalgam (2.5 g) was added under ice cooling with stirring to a suspension of 120 mg (0.147 mmole) of the hydroxysulfone (8a) and 0.5 g of sodium dihydrogen phosphate in 1.5 ml of methanol and 6 ml of tetrahydrofuran. The mixture was stirred for 1.5 hours. The reaction mixture was extracted in a customary manner, and then purified by medium-pressure liquid column chromatography (n-hexane:ethyl acetate=15:1 v/v) to give 68 mg of the captioned compound (9a).

By a similar procedure, 55 ng of compound (9b) was prepared from 150 mg of the compound (8b); 67 mg of compound (9b) from 131 mg of the compound (8c); and 32 mg of compound (9a) from 111 mg of the compound (8d).

Compound (9a) (colorless crystals)

IRν$_{max}$$^{KBr}$ cm$^{-1}$: 2950, 1450, 1210, 1020.

$^1$H-NMR (CDCl$_3$) δ: 0.62(3H, s), 0.93(3H, s), 1.02(3H, d, J=6.6Hz), 1.21(1H, d, J=7.0Hz), 2.93(1H, m), 3.47(3H, s), 3.48(1H, m), 3.62(1H, m), 3.91(1H, m), 4.72(1H, m), 4.90, 5.00(2H, dx2, J$_{gem}$=6.5Hz), 5.36(1H, m), 5.40(2H, m), 5.54(1H, m).

$^{19}$F-NMR (CDCl$_3$) δ: −5.65(s).

MS m/e: 564(M+-pyranyl), 546(M+-pyranyl, H$_2$O), 530, 505.

High resolution MS: for C$_{30}$H$_{40}$F$_6$O$_2$(M+-pyranyl, H$_2$O): Calculated: 546.2930; Found: 546.2971

Compound (9b) (colorless crystals)

IRν$_{max}$$^{KBr}$ cm$^{-1}$: 2950, 1450, 1210, 1025.

$^1$H-NMR (CDCl$_3$) δ: 0.61(3H, s), 0.93(3H, s), 1.02(3H, d, J=6.6Hz), 1.21 3H, d, J=6.9Hz), 2.93(1H, m), 3.47(3H, s), 3.48(1H, m), 3.62(1H, m), 3.91(1H, m), 4.72(1H, m), 4.89, 4.99(2H, dx2, J$_{gem}$=6.4Hz), 5.37(3H, m), 5.54(1H, m).

$^{19}$F-NMR (CDCl$_3$) δ: −5.57(s).

MS m/e: 564(M+-pyranyl), 546(M+-pyranyl, H$_2$O), 531, 505.

High resolution MS: for C$_{30}$H$_{40}$F$_6$O$_2$(M+-pyranyl, H$_2$O): Calculated: 546.2930; Found: 546.2958

(h) Production of 26,26,26,27,27,27-hexafluoro-ergosta-5,7,22(E)-triene-3β,25-diol 25-methoxymethyl ether (9a', 9b'):

Under an argon atmosphere, 10 mg of p-toluenesufonic acid was added to a solution of 97.2 mg (0.150 mmole) of the compound (9a) in 4.5 ml of methylene chloride and 4.5 ml of methanol, and the mixture was stirred at room temperature for 1.5 hours. Aqueous sodium bicarbonate solution was added to the reaction mixture, and the mixture was extracted with ether. The ether extract was washed with aqueous sodium chloride solution, dried over anhydrous magnesium sulfate, and purified by medium-pressure liquid column chromatography (n-hexane:ethyl acetate=4:1 v/v) to give 81.5 mg of the captioned compound (9a').

By a similar procedure, 108 mg of compound (9b') was prepared from 134 mg of the compound (9b).

Compound (9a') (colorless crystals)

IRν$_{max}$$^{KBr}$ cm$^{-1}$: 3410, 2940, 1215, 1050, 720.

$^1$H-NMR (CDCl$_3$) δ: 0.63(3H, s), 0.94(3H, s) 1.03(3H, d, J=6.6Hz), 1.20(3H, d, J=7.0Hz), 2.28(1H, m), 2.46(1H, m), 2.93(1H, m), 3.48(3H, s), 3.63(1H, m), 4.91, 5.01(2H, dx2, J$_{gem}$=5Hz), 5.38(1H, m), 5.40(2H, m), 5.56(1H, dd, J=5.5Hz, 2.2Hz).

$^{19}$F-NMR (CDCl$_3$) δ: −5.63(s).

MS m/e: 564(M+), 531(M+-H$_2$O, CH$_3$), 505.

High resolution MS: for C$_{30}$H$_{42}$F$_6$O$_3$(M+): Calculated: 564.3035; Found: 564.3017

Compound (9b') (colorless crystals)

IRν$_{max}$$^{KBr}$ cm$^{-1}$: 3460, 2950, 1215, 1050, 720.

$^1$H-NMR (CDCl$_3$) δ: 0.63(3H, s), 0.94(3H, s), 1.02(3H, d, J=6.6Hz), 1.21(3H, d, J=7.0Hz), 2.28(1H, m), 2.46(1H, m), 2.93(1H, m), 3.48(3H, s), 3.63(1H, m), 4.90, 5.00(2H, dx2, J$_{gem}$=4Hz), 5.38(3H, m), 5.56(1H, dd, J=5.5Hz, 2.3Hz).

$^{19}$FNMR (CDCl$_3$) δ: −5.50(s).

MS m/e: 564(M+), 531(M+-H$_2$O, CH$_3$), 505.

High resolution MS: for C$_{30}$H$_{42}$F$_6$O$_3$(M+): Calculated: 564.3036; Found: 564.3043

(i) Production of 26,26,26,27,27,27-hexafluoro-ergosta-5,7-22(E)-triene-3β,25-diol (10a, 10b):

Under an argon atmosphere, a solution of 50.6 mg (0.091 mmole) of the compound (9a') and 10 mg of p-toluenesulfonic acid in 3 ml of methylene chloride and 3 ml of methanol was heated under reflux for 3 hours while shutting off light. The reaction mixture was extracted in a customary manner and purified by medium-pressure liquid column chromatography (n-hexane:ethyl acetate=3:1 v/v) to give 35.1 mg of the captioned compound (10a).

By a similar procedure, 48.2 mg of compound (10b) was prepared from 68.7 mg of the compound (9b').

Compound (10a) (colorless crystals)

IRν$_{max}$$^{KBr}$ cm$^{-1}$: 3520, 3220, 2950, 1210, 980 930, 715.

$^1$H-NMR (CDCl$_3$) δ: 0.65(3H, s), 0.95(3H, s), 1.08(3H, d, J=6.6Hz), 1.28(3H, d, J=5.8Hz), 2.28(1H, m), 2.47(1H, m), 2.77(1H, m), 3.05(1H, s), 3.64(1H, m), 5.27-5.36(1H, m), 5.39(1H, m), 5.57(1H, m), 5.59(1H, dd, J=15.2Hz, 9.0)Hz).

$^{19}$F-NMR (CDCl$_3$) δ: −8.78(q, J=9Hz), −9.75(q, J=9Hz).

MS m/e: 520(M+), 487(M+-H$_2$O, CH$_3$), 460.

High resolution MS: for C$_{28}$H$_{38}$F$_6$O$_2$(M+): Calculated: 520.2773; Found: 520.2756

Compound (10b) (colorless crystals)

IRν$_{max}$$^{KBr}$ cm$^{-1}$: 3400, 2940, 1210, 980, 925, 715.

$^1$H-NMR (CDCl$_3$) δ: 0.63(3H, s), 0.95(3H, s), 1.08(3H, d, J=6.6Hz), 1.28(3H, d, J=6.8Hz), 2.28(1H, m), 2.47(1H, m), 2.78(1H, m), 5.39(1H, m), 5.57(1H, m), 5.60(1H, dd, J=15.4Hz, 8.7Hz).

$^{19}$F-NMR (CDCl$_3$) δ: −8.56(q, J=9Hz), −9.82(q, J=9Hz).

MS m/e: 520(M+), 487(M+-H$_2$O, CH$_3$), 461.

High resolution MS: for $C_{28}H_{38}F_6O_2(M^+)$: Calculated: 520.2774; Found: 520.2814

(j) Production of 26,26,26,27,27,27-hexafluoro-25-hydroxyvitamin $D_2$:

Under an argon atmosphere, a solution of 7.73 mg (0.015 mmole) of the compound (10a) in 40 ml of ethanol and 90 ml of benzene was irradiated for 5 minutes with light from a medium-pressure mercury lamp (200 W) using a Bicol filter, and then heated under reflux for 1 hour. Under reduced pressure, the solvent was concentrated, and the residue was subjected to thin-layer chromatography (kiesel gel 60F254, Merck Co.; thickness 0.25 mm) and developed five times with benzene:ethyl acetate (10:1, v/v) to give 2.28 mg of one isomer (Rf=0.40) of the captioned compound.

UV (EtOH): $\lambda_{max}=264.5$ nm, $\lambda_{min}=228$ nm

MS m/e: 520(M+), 502(M+-H$_2$O), 487 (M+-CH$_3$), 271, 253, 136, 118

HPLC (Zorbax SIL, 5% isopropanol-hexane, 2.0 ml/min.): Retention time: 5.4 min.

By repeating the above procedure except that 11.74 mg (0.023 mmole) of the compound (10b) was used instead of the compound (10a), 2.90 mg of the other isomer of the captioned compound was obtained.

UV (EtOH): $\lambda_{max}=264.5$ nm, $\lambda_{min}=228$ nm

HPLC (Zorbax SIL, 5% isopropanol-hexane, 2.0 ml/min.): Retention time: 5.1 min.

EXAMPLE 2

Production of 28-nor-26,26,26,27,27,27,-hexafluoro-25-hydroxyvitamin $D_2$ [$R^1=CF_3$, $R^2=H$ in formula (1)] (reaction scheme B):

Production of 26,26,26,27,27,27-hexafluoro-23-phenylsulfonylcholesta-5,7-diene-3β,22,25-triol 25-methoxymethyl 3β-tetrahydropyranyl diether (12a, 12b):

Under an argon atmosphere, 0.54 ml (0.73 mmole) of n-butyllithium (1.35M hexane solution) was added to a solution 102 microliters (0.73 mmole) of diisopropylamine in 2 ml of tetrahydrofuran at −78° C. (over a dry ice-acetone bath), and the mixture was stirred for 5 minutes. In the same manner as in Example 1, (a) to (e), a solution of 277 mg (0.73 mmole) of 4-phenylsulfonyl-1,1,1-tri-fluoro-2-trifluoromethylbutane-2-ol 2-methoxymethyl ether (11) obtained from ethyl acetoacetate in 2 ml of tetrahydrofuran. Under ice cooling, the mixture was stirred for 30 minutes. The reaction mixture was cooled to −78° C., and a solution of 201 mg (0.40 mmole) of 22,23-bisnor-3β-tetrahydropyranyloxychol-5,7-dien-22-al (7) in 2 ml of tetrahydrofuran was added. The mixture was stirred for 1.5 hours. The reaction mixture was extracted in a customary manner, and purified by silica gel column chromatography (70 g; n-hexane:ethyl acetate=8:1-3:1 v/v) to give diastereomers of the captioned compounds (12a) (83 mg) and (12b) (235 mg) in the sequence of elution.

Compound (12a) (amorphous compound)

IR$\nu_{max}^{KBr}$ cm$^{-1}$: 3500, 2940, 1450, 1220, 1150, 1130, 1025, 980.

$^1$H-NMR (CDCl$_3$) δ: 0.54(3H, s), 3.47(3H, s), 3.48(1H, m), 3.94(1H, m), 4.74(1H, m), 5.03(2H, m), 5.38(1H, m), 5.56(1H, m), 7.57-7.96(5H, m).

MS m/e: 708(M+-pyranyl), 690(M+-pyranyl, H$_2$O), 675.

Compound (12b) (amorphous compound)

IR$\nu_{max}^{KBr}$ cm$^{-1}$: 3480, 2950, 1450, 1225, 1135, 1030, 980.

$^1$H-NMR (CDCl$_3$) δ: 0.60(3H, s), 0.92(3H, d, J=5.4Hz), 0.93(3H, s), 3.42(3H, s), 3.49(1H, m), 3.63(1H, m), 3.79(1H, m), 3.94(1H, m), 4.74(1H, m), 4.99(2H, s), 5.38(1H, m), 5.56(1H, m), 7.54-7.96(5H, m).

MS m/e: 708(M+-pyranyl), 690(M+-pyranyl, H$_2$O), 675.

(b) Production of 26,26,26,27,27,27-hexafluoro-23-phenylsulfonylcholesta-5,7-diene-3β, 22,25-triol 25-methoxymethyl 3β-tetrahydropyranyl diether: 22-acetate (13):

Under an argon atmosphere, a methylene chloride (3 ml) solution of 227 mg (0.29 mmole) of the compound (12b), 10 mg of 4-dimethylaminopyridine, 0.46 ml (5.7 mmoles) of pyridine and 0.27 ml (2.9 mmoles) of acetic anhydride was stirred at room temperature for 20 hours while shutting off light. The reaction mixture was poured into 1N hydrochloric acid and extracted with ether. The ether extract was washed with saturated aqueous sodium bicarbonate solution and then with aqueous sodium chloride solution, and dried over anhydrous magnesium sulfate. The solvent was evaporated under reduced pressure, and the residue was purified by silica gel column chromatography (40 g; n-hexane:ethyl acetate=5:1 v/v) to give 216 mg of the captioned compound (13) as an amorphous compound.

IR$\nu_{max}^{KBr}$ cm$^{-1}$: 2950, 1740, 1450, 1225, 1160, 1135, 1030, 980.

$^1$H-NMR (CDCl$_3$) δ: 0.64(3H, s), 0.93(3H, s), 1.13(3H, d, J=6.4Hz), 2.03(3H, s), 3.36(3H, s), 3.49(1H, m), 3.63(1H, m), 3.85(1H, m), 3.93(1H, m), 4.74(1H, m), 4.75, 4.89(2H, dx2, $J_{gem}$=6.0Hz), 5.38(1H, m), 5.50(1H, dd, J=5.1Hz, 2.0Hz), 5.56(1H, m), 7.55-7.92(5H, m).

MS m/e: 834(M+), 832, 732(M+-pyranyl, H$_2$O), 687.

(c) Production of 26,26,26,27,27,27-hexafluorocholesta-5,7-22(E)-triene-3β,25-diol 25-methoxymethyl 3β-tetrahydropyranyl diether (14):

Under an argon atmosphere, 1.5 g of 5% sodium amalgam was added to a suspension of of 211 mg (0.25 mmole) of the compound (13) and 760 mg of of disodium hydrogen phosphate in 4.5 ml of tetrahydrofuran and 1.5 ml of methanol, and the mixture was stirred at room temperature for 2 hours. The reaction mixture was diluted with ether. The precipitate was separated by filtration on Celite. The filtrate was washed with aqueous sodium chloride solution, and dried over anhydrous magnesium sulfate. The solvent was evaporated under reduced pressure, and the residue was purified by silica gel column chromatography (40 g; n-hexane:ethyl acetate=10:1 v/v) to give 117 mg of the captioned compound (14) as colorless crystals.

IR$\nu_{max}^{KBr}$ cm$^{-1}$: 2940, 1450, 1205, 1025, 975, 720.

$^1$H-NMR (CDCl$_3$) δ: 0.63(3H, s), 0.94(3H, s), 1.04(3H, d, J=6.6Hz), 2.80(2H, d, J=6.8Hz), 3.46(1H, s), 3.49(1H, m), 3.64(1H, m), 3.93(1H, m), 4.74(1H, m), 4.96 4.97(2H, dx2, $J_{gem}$=7.2Hz), 5.38(2H, m), 5.50(1H, dd, J=15.2Hz, 8.78Hz), 5.56(1H, m).

MS m/e: 634(M+), 632, 532(M+-pyranyl, H$_2$O).

(d) Production of 26,26,26,27,27,27-hexafluorocholesta-5,7,22(E)-triene-3β, 25-diol (15):

Under an argon atmosphere, 15 mg of p-toluenesulfonic acid was added to a solution of 68 mg (0.11 mmole) of the compound (14) in 3 ml of methylene chloride and 3 ml of methanol, and the mixture was heated under reflux for 14 hours while shutting off light. The reaction mixture was poured into saturated aqueous sodium bicarbonate solution, and extracted with ether. The ether extract was washed with aqueous sodium chloride solution, and dried over anhydrous magnesium sulfate. The solvent was evaporated under reduced pressure. The residue was purified by medium-pressure liquid column chromatography (n-hexane:ethyl acetate=5:1 v/v) to give 20 mg of the captioned compound (15) as colorless crystals.

IR$\nu_{max}^{KBr}$ cm$^{-1}$: 3270, 2940, 1455, 1210, 1140, 1050, 1025, 970.

$^1$H-NMR (CDCl$_3$) δ: 0.65(3H, s), 0.95(3H, s), 1.09(3H, d, J=6.7Hz), 2.20(1H, m), 2.28(1H, m), 2.47(1H, m), 2.64, 2.66(2H, ddx2, J$_{gem}$=14.6Hz, 7.6Hz), 2.98(1H, s), 3.64(1H, m), 5.36(1H, dt, J=15.3Hz, 7.6Hz), 5.39(1H, m), 5.57(1H, m), 5.62(1H, dd, J=15.3Hz, 8.8Hz).

$^{19}$F-NMR (CDCl$_3$) δ: −13.73(q, J=9Hz), −14.04(q, J=9Hz).

MS m/e: 506(M$^+$), 473(M$^+$-H$_2$O, CH$_3$), 447.

High resolution MS: for C$_{28}$H$_{31}$F$_6$O(M$^+$-H$_2$O, CH$_3$): Calculated: 473.2277; Found: 473.2285

(e) Production of 28-nor-26,26,26,27,27,27-hexafluoro-25-hydroxyvitamin D$_2$:

The residue obtained by treating 7.75 mg (0.014 mmole) of the compound (15) in the same way as in Example 1, (j) was subjected to thin-layer chromatography (kiesel gel 60F254, Merck Co.; thickness 0.25 mm) and developed twice with benzene:ethyl acetate=20:1 v/v to give 1.53 mg of the captioned compound having an Rf value of 0.31.

UV (EtOH): λ$_{max}$=264 nm, λ$_{min}$=228 nm

MS m/e: 506(M$^+$), 473(M$^+$-H$_2$O, CH$_3$), 271, 253, 136, 118.

HPLC (Zorbax SIL, 5% isopropanol/n-hexane, 2.0 ml/min.): Retention time: 5.6 min.

EXAMPLE 3

Production of (24ξ)-28,28,28-trifluoro-25-hydroxyvitamin D$_2$ [R$^1$=CH$_3$,R$^2$=CF$_3$ in formula (1)](reaction scheme C):

(a) Production of 2-methyl-4-phenylsulfonyl-2-triethylsiloxy-3-trifluoromethylbutyric acid ethyl ester (17):

Under an argon atmosphere, 4.62 ml (6.9 mmoles) of n-butyllithium (1.4M hexane solution) was added to a solution of 0.96 ml (6.8 mmoles) of diisopropylamine in 10 ml of tetrahydrofuran at −78° C. (over a dry ice-acetone bath), and the mixture was stirred for 20 minutes. Then, a solution of 1.404 g (6.04 mmoles) of ethyl α-triethylsiloxypropionate (16) in 5 ml of tetrahydrofuran was added, and the mixture was stirred for 1 hour. A solution of 1.18 g (5.0 mmoles) of 1-phenylsulfonyl-3,3,3-trifluoropropene in 10 ml of tetrahydrofuran was added to the resulting solution, and the mixture was stirred for 30 minutes. The reaction mixture was poured into ice water, and extracted with ether. The ether extract was washed with aqueous sodium chloride solution and dried over anhydrous magnesium sulfate. The solvent was evaporated under reduced pressure, and the residue was subjected to silica gel column chromatography, and 2.15 g of a diastereomeric mixture of the captioned compound (17) was obtained from the eluates obtained with n-hexane:ethyl acetate (9:1, v/v) as a colorless oil.

IR$\sigma_{max}^{CCl_4}$ cm$^{-1}$: 2950, 2880, 1750, 1450, 1300, 1150, 1080, 730.

$^1$H-NMR (CDCl$_3$) δ: 0.42-1.07(15H, m), 1.29 and 1.30(3H, each t, J=7Hz), 1.53(3H, s), 3.10-3.83(3H, m), 4.19 and 4.20(2H, each q, J=7Hz), 7.43-8.05(5H, m)

$^{19}$F-NMR (CDCl$_3$) δ: −1.33(d, J=8Hz), +0.5(d, J=8Hz).

MS m/e: 439(M$^+$-C$_2$H$_5$), 395(M$^+$-CO$_2$C$_2$H$_5$), 365(M$^+$-CO$_2$C$_2$H$_5$, C$_2$H$_5$, H).

High resolution MS: for C$_{18}$H$_{26}$F$_3$O$_5$SSi(M$^+$-C$_2$H$_5$): Calculated: 439.1217; Found: 439.1220

(b) Production of 2-methyl-4-phenylsulfonyl-3-trifluoromethylbutane-1,2-diol (18):

Under an argon atmosphere, 53 ml (63.1 mmoles) of diisobutyl aluminum hydride (1.19M hexane solution) was added in two divided portions at two different times under ice cooling to a solution of 5.95 g (12.7 mmoles) of the compound (17) in 35 ml of ether, and the mixture was stirred for 70 minutes. The reaction mixture was mixed with water and 1N aqueous sodium hydroxide solution, and extracted with ether. The extract was washed with 1N aqueous sodium hydroxide solution and aqueous sodium chloride solution, and dried over anhydrous magnesium sulfate. The solvent was concentrated under reduced pressure. The residue was dissolved in methanol, and 0.5 ml of concentrated hydrochloric acid was added. The mixture was stirred at room temperature for 2.5 hours. The reaction mixture was concentrated under reduced pressure, and the residue purified by silica gel column chromatography (100 g; n-hexane:ethyl acetate=1:1 v/v) to give 3.90 g of a diastereomeric mixture of the captioned compound (18) as a colorless oil.

IR$\nu_{max}^{CCl_4}$ cm$^{-1}$: 3700-3100, 3000, 2950, 1450, 1370, 1150, 1080, 740.

$^1$H-NMR (CDCl$_3$) δ: 1.20(3H, bs), 1.33(3H, s), 2.87(2H, bs), 3.30-3.93(5H, m), 7.47-8.07(5H, m).

$^{19}$F-NMR (CDCl$_3$) δ: +0.3(d, J=9Hz), +0.6(q, J=9Hz).

MS m/e: 295(M$^+$-OH), 281(M$^+$-CH$_2$OH).

High resolution MS: for C$_{12}$H$_{14}$F$_8$O$_3$S(M$^+$-OH): Calculated: 245.0619; Found: 295.0615

(c) Production of 2-methyl-4-phenylsulfonyl-3-trifluoromethyl-1,2-epoxybutane (19):

Under an argon atmosphere, 1.45 ml (18.7 mmoles) of methanesulfonyl chloride was added under ice cooling to a solution of 3.90 g (12.5 mmoles) of the compound (18) and 6.10 ml (43.8 mmoles) of triethylamine in 25 ml of methylene chloride, and the mixture was stirred for 3.5 hours while the temperature was being returned to room temperature. To the reaction mixture was added 5.60 ml (37.4 mmoles) of 1,8-diazabicyclo[5,4,0]-7-undecene, and the mixture was stirred for 2.5 hours. The reaction mixture was poured into ice-dilute hydrochloric acid, and extracted with ether. The ether extract was washed with saturated aqueous sodium bicarbonate solution and aqueous sodium chloride solution, dried over anhydrous magnesium sulfate, and concentrated under reduced pressure. The residue was purified by silica gel column chromatography (150 g; n-hexane:ethyl acetate=5:1 to 3:1 v/v) to give 3.02 g of the captioned compound (19) as a colorless oil.

IR$\nu_{max}^{CCl_4}$ cm$^{-1}$: 3000, 2950, 1450, 1310, 1150, 1080, 910, 750.

$^1$H-NMR (CDCl$_3$) δ: 1.37(3H, s), 1.42(3H, s), 2.62-3.10(3H, m), 3.38(1H, d, J=16.5Hz), 3.44(1H, d, J=16.5Hz), 7.55-8.33(5H, m).

$^{19}$F-NMR (CDCl$_3$) δ: −2.5(d, J=9Hz), −2.7(d, J=9Hz).

MS m/e: 295(M++1), 264(M+-CH₂O), 230, 198, 153(M+-phenylsulfonyl).

High resolution MS: for $C_{12}H_{14}F_3O_3S$(M++1): Calculated: 295.0589; Found: 295.0614

(d) Production of 2-methyl-4-phenylsulfonyl-3-trifluoromethyl-2-butanol (20):

Under an argon atmosphere, a solution of 1.366 g (4.64 mmoles) of the compound ($^{19}$) in 17 ml of ether was gradually added under ice cooling to a suspension of 0.18 g (4.74 mmoles) of lithium aluminum hydride in 10 ml of ether, and the mixture was stirred for 1 hour. Water and dilute hydrochloric acid were added to the reaction mixture, and then the mixture was extracted with ether. The ether extract was washed with aqueous sodium chloride solution, and dried over anhydrous magnesium sulfate. The solvent was evaporated under reduced pressure, and the residue was purified by silica gel column chromatography (80 g; n-hexane:ethyl acetate=3:1 v/v) to give 1.354 g of the captioned compound (20) as colorless crystals.

Melting point: 59°-60° C. (recrystallized from ether/methylene chloride/n-hexane)

IR$\nu_{max}^{KBr}$ cm$^{-1}$: 3520, 3010, 1300, 1160, 1130, 740, 690.

$^1$H-NMR (CDCl₃) δ: 1.29(3H, bs), 1.49(3H, s), 2.50(1H, bs), 3.00(1H, qd, J=9.8Hz, 4.5Hz), 3.33(1H, dd, $J_{gem}$=15Hz, 4.5Hz), 3.77(1H, dd, J , 4.5Hz), 7.53-8.22(5H, m). $^{19}$F-NMR (CDCl₃) δ: −0.83(d, J=10Hz).

MS m/e: 296(M+), 281(M+-CH₃), 200.

Elemental analysis for $C_{12}H_{15}F_3O_3S$: Calculated: C:48.64, H:5.10, F:$^{19.24}$, S:10.82; Found: C:48.54, H:5.13, F:$^{19.01}$, S:10.54

(e) Production of 2-methyl-4 phenylsulfonyl-3-trifluoromethyl-2-butanol tetrahydropyranyl ether (21):

While under an argon atmosphere, 1.65 ml (18.09 mmoles) of 2,3-dihydropyrane and 30 ml of p-toluenesulfonic acid, in three divided portions, were added at three different times to a solution of 1.337 g (4.51 mmoles) of the compound (20) in 17 ml of 1,4-dioxane, the mixture was stirred at room temperature for 24 hours. The reaction mixture was poured into ice/1N aqueous solution of sodium hydroxide, and extracted with ether. The ether extract was washed with aqueous sodium chloride solution, and dried over anhydrous magnesium sulfate, and the solvent was evaporated under reduced pressure. The residue was purified by silica gel column chromatography (100 g; n-hexane/ethyl acetate=4:1 v/v) to give 1.274 g of the captioned compound (21) as a colorless oil.

IR$\nu_{max}^{CHCl3}$ cm$^{-1}$: 2950, 1450, 1310, 1160, 1100, 1030, 990.

$^1$H-NMR (CDCl₃) δ: 1.33(3H, s), 1.41, 1.44(3H, sx2), 3.07(1H, m), 3.36(1H, m), 3.46(1H, m), 3.73(1H, m), 3.88(1H, m), 4.83(1H, m), 7.55-7.96(5H, m).

$^{19}$F-NMR (CDCl₃) δ: −0.47(d, J=9Hz).

MS m/e: 381(M++1), 279(M+-pyranyl, OH), 259(M+-pyranyl, OH, HF).

High resolution MS: for $C_{12}H_{13}F_2O_2S$(M+-pyranyl, OH, HF): Calculated: 259.0603; Found: 259.0618

(f) Production of 23-phenylsulfonyl-28,28,28-trifluoroergosta-5,7-diene-3β,22,25-triol 3β,25-bistetrahydropyranyl ether (22):

By operating in the same way as in Example 1, (f), 257 mg of the captioned compound (22) as an amorphous compound was prepared from 208 mg (0.55 mmole) of the compound (21) and 151 mg (0.355 mmole) of 22,23-bisnor-3β-tetrahydropyranyloxychol-5,7-dien-22-al (7).

IR$\nu_{max}^{KBr}$ cm$^{-1}$: 3450, 2940, 1140, 1070, 1030.

$^1$H-NMR (CDCl₃) δ: 0.56, 0.59(3H, sx2), 0.79, 0.84(3H, dx2, J=6.7Hz), 5 37(1H, m), 5.54(1H, m), 7.50-7.96(5H, m). $^{19}$F-NMR (CDCl₃) δ: +7.54(d, J=11Hz).

MS m/e: 690(M+-pyranyl, H₂O), 606(M+-2 x pyranyl, H₂O), 548(M+-pyranyl, H₂O, phenylsulfonyl-H), 311, 279.

(g) Production of 28,28,28-trifluoroergosta5,7,22(E)-triene-3β,25-diol 3β,25-bistetrahydropyranyl ether (23):

By operating in the same way as in Example 1, (g), 132 mg of the captioned compound (23) as colorless crystals was prepared from 272 mg (0.343 mmole) of the compound (22).

IR$\nu_{max}^{KBr}$ cm$^{-1}$: 2940, 1255, 1090, 1020.

$^1$H-NMR (CDCl₃) δ: 0.62(3H, s), 0.93(3H, s), 1.05(3H, d, J=6.6Hz), 2.75(1H, m), 3.46(3H, m), 3.61(1H, m), 3.91(2H, m), 4.72(1H, m), 4.86(1H, m), 5.28(1H, m), 5.36(1H, m), 5.47(1H, m), 5.53(1H, d, J=5.4Hz).

$^{19}$F-NMR (CDCl3) δ: −0.11(m).

MS m/e: 634(M+), 632, 532(M+-pyranyl, H₂O), 447.

(h) Production of 28,28,28-trifluoroergosta-5,7,22(E)-triene-3β,25-diol (24):

By operating in the same wa/ as in Example 1, (h), 94 mg of the captioned compound (24) as colorless crystals was prepared from 132 mg (0.208 mmole) of the compound (23).

IR$\nu_{max}^{KBr}$ cm$^{-1}$: 3420, 2940, 1250, 1086.

$^1$H-NMR (CDCl₃) δ: 0.638, 0.644(3H, sx2), 0.94(3H, s), 1.08(3H, d, J=6.6Hz), 1.27, 1.32(6H, sx2), 2.17(1H, m), 2.720, 2.726(1H, quint x 2, J=9.7Hz), 3.63(1H, m), 5.319(1H, dd, J=15.2Hz, 9.9Hz), 5.333(1H. dd, J=15.5Hz, 9.9Hz), 5.38(1H, m), 5.57(1H, m), 5.59(1H, dd, J=15.1Hz, 8.7Hz), $^{19}$F-NMR (CDCl₃) δ: −0.87(d, J=10Hz), −1.04(d, J=10Hz).

MS m/e: 466(M+), 433(M+-CH , H₂O), 407, 338, 253.

High resolution MS: for $C_{28}H_{41}F_3O_2$(M+): Calculated: 466.3055; Found: 466.3026

(i) Production of (24ξ)-28,28,28-trifluoro-25-hydroxyvitamin D₂:

By operating in the same way as in Example 1, (j), 2.8 mg of the captioned compound was prepared from 8.8 mg (18.9 mmoles) of the compound (24).

UV (EtOH): $\lambda_{max}$=265 nm, $\lambda_{min}$=228 nm

MS m/e: 466(M+), 433(M+-CH₃, H₂O), 271, 253, 136, 118, 59.

HPLA (Zorbax SIL, 5% isopropanol/n-hexane, 2.0 ml/min.): retention time 5.7 min.

The fluorine-containing vitamin D₂ derivatives of formula (1) provided by this invention have strong antiosteoporotic activity and yet low bone salt dissolving activity, and are expected to be useful as drugs for preventing and treating bone diseases such as osteoporosis, nephropathy and parathyropathy, and diseases such as rheumatoid arthritis, proriasis and cancer.

The excellent pharmacological activity of the compounds of this invention can be demonstrated by the following animal tests. In these tests, the following compounds was obtained.

Compound I: one isomer of 26,26,26,27,27,27-hexafluoro-25-hydroxyvitamin D₂ $R_1=CF_3$, $R_2=CH_3$ in formula (1)]

Compound II: the other isomer of compound I

Compound III: (24ξ)-28,28,28-trifluoro-25-hyhdroxyvitamin D₂ $R_1=CF$ , $R_2=H$ in formula (1)]

Compound IV: 1β,25-dihydroxyvitamin $D_3$ (comparison)

Compound V: 26,26,26,27,27,27-hexafluoro-25-dihydroxyvitamin $D_3$ (comparison)

TEST EXAMPLE 1

Bone mineral dissolving activity (liberation of calcium from bones:

Testing procedure

Wistar-strain male rats (3 weeks old) were fed with a vitamin D-deficient low calcium feed (Ca: 0.02%, P: 0.3%). An ethanol solution (0.05 ml) of each of the test compounds was intravenously administered to the rats, and 24 hours later, blood was drawn from the abdominal main artery of the animals under ether anesthesia. The blood was centrifuged at 3,000 rpm for 10 minutes to obtain serum samples. The amount of calcium in the serum samples was measured by a double beam atomic absorption photometer (Model AA-650 made by Shimazu Seisakusho). The data given for compounds IV and V are those given in Y. Tanaka, H. F. DeLuca, Y. Kobayashi and N. Ikekawa: Arch. Biochem. Biophys., 228, 348 (1984).

Results

The results are shown in Table 1. It is seen from Table 1 that while the percent increase of the calcium concentration in the blood was 25.2 and 52.6% for compounds IV and V, it was as low as 9.3, 9.3 and 14.0% for compounds I, II and III, respectively. These results show that compounds I, II and III have low bone salt dissolving activity, and suggest their weak side-effects.

TABLE 1

| Run No. | Test compound | Dose (p moles/kg) | Ca concentration in blood (mg/dl) | Percent increase (%) (**) |
|---|---|---|---|---|
| 1 (*) | None (control) | 0 | 3.8 | 0 |
|  | IV | 650 | 4.8 | 26.3 |
|  | V | 650 | 5.8 | 52.6 |
| 2 | None (control) | 0 | 4.3 | 0 |
|  | I | 650 | 4.7 | 9.3 |
|  | II | 650 | 4.7 | 9.3 |
|  | III | 650 | 4.9 | 14.0 |

(*): The data given were cited from Y. Tanaka et al., Arch. Biochem. Biophys., 229, 348 (1984).

(**): Calculated in accordance with the following equation.

$$\text{Percent increase} = \frac{\left(\begin{array}{c}\text{Concentration of Ca in blood in the group to which the test compound was administered}\end{array}\right) - \left(\begin{array}{c}\text{Concentration of Ca in blood in the control group}\end{array}\right)}{\left(\begin{array}{c}\text{Concentration of Ca in blood in the control group}\end{array}\right)} \times 100$$

TEST EXAMPLE 2

Antiosteoporotic activity:

Testing procedure

A surgical operation was performed on Wistar-strain female rats (9 to 10 months old) to remove the ovary and cut the right sciatic nerve. Each test compound was administered in a dose of 300 p moles/kg four times a week. As a control, ethanol alone was administered. Beginning with the day next to the day of operation, the test compound was administered over 2 weeks. The animals were sacrificed 24 hours after the final administration. The tibia was extracted and fixed with 70% ethanol.

The tibia was stained by villanueva's bone stain and embedded in methyl methacrylate. The specimen was cut with a circular saw in the frontal plane and thinned to about 20–25μm thickness with a gliding scrubber. Histomorphometric measurement was done with a digitizer (MUTO-ID$_{20}$BL) connected to a personal computer (Cannon AS-100M).

The trabecular bone area was measured and then the trabecular bone specific volume was calculated.

Results

The results are shown in Table 2. As demonstrated by the results, an antiosteoporotic effect was observed in any one of the test compounds including the comparative compounds IV and V. However, in terms of percent increases in the trabecular bone specific volume, compounds I, II and III in accordance with the present invention showed an increase of about 200%, which is higher than that of the comparative compound IV and is comparable to that of the comparative compound V.

TABLE 2

| Run No. | Test compound | Trabecular bone specific volume mm³/mm³ | Percent increase (%) (*) |
|---|---|---|---|
| 1 | None (control) | 4.5 | 0 |
|  | V | 16.1 | 258.8 |
| 2 | None (control) | 5.1 | 0 |
|  | IV | 10.2 | 100.0 |
|  | I | 15.4 | 202.0 |
|  | II | 15.2 | 198.0 |
|  | III | 16.8 | 229.4 |

(*): Calculated in accordance with the following equation.

$$\text{Percent increase} = \frac{\left(\begin{array}{c}\text{Trabecular bone specific volume in the group to which test compound was administered}\end{array}\right) - \left(\begin{array}{c}\text{Trabecular bone specific volume in the control group}\end{array}\right)}{\left(\begin{array}{c}\text{Trabecular bone specific volume in the control group}\end{array}\right)} \times 100$$

The results of Test Examples 1 and 2 are summarized in Table 3.

TABLE 3

| Vitamin D derivative | Relative activity Bone salt dissolving activity (A)* | Antiosteoporotic activity (B)** | Degree of separation (B)/(A)*** |
|---|---|---|---|
| IV | 1.00 | 1.00 | 1.00 |
| V | 2.00 | 2.58 | 1.29 |
| I | 0.35 | 2.02 | 5.77 |
| II | 0.35 | 1.98 | 5.66 |
| III | 0.53 | 2.29 | 4.32 |

*The percent increase of the calcium concentration in blood in Table 1 expressed relatively by taking that of compound IV as 1.00.

**The percent increase of the trabecular bone specific volume in Table 2 expressed relatively by taking that of compound IV as 1.00.

***The degree to which the bone mineral dissolving activity (side-effect) separates from the antiosteoporotic activity (pharmacological efficacy). It is expressed by the ratio of (A) to (B). Larger values show better separation.

The fluorine-containing vitamin $D_2$ derivatives of formula (1) provided by this invention, for example compounds I, II and III indicated hereinabove have a bone mineral dissolving activity (bone calcium liberating activity) of 0.35, 0.35 and 0.53 (when that of compound IV is taken as 1.00) in rats fed with a vitamin D-deficient low calcium-containing feed which are lower than those of comparative compounds IV and V (1.00 and 2.00 respectively). This fact suggest that the compounds of formula (1) provided by the present invention have weak side-effects and strong antiosteoporotic activity with an excellent balance between their bone-forming activity and bone mineral dissolving activity.

In a rat osteopososis model obtained by ovariectony and cutting the sciatic nerve, compound V shows a strong antiosteoporotic effect of 2.5H when that of compound IV is taken as 1.00 (see Table 3). The compounds I, II and III in accordance with this invention a strong antiosteoporotic effect even when the relative values are 2.02, 1.98 and 2.29 which are smaller than 2.58. The degree of separation (antiosteoporotic activity/bone mineral dissolving activity) is 5.07 for compound I, 5.66 for compound II and 4.32 for compound III which are larger than 1.00 for compound IV and 1.29 for compound V. Hence, the separation of these activity is excellent in the compounds of this invention.

Accordingly, the compounds of this invention are considered as useful as a medicament for prevention and/or treatment of diseases such as calcium pathobolism and osteoporosis.

For use as a medicament for the prevention and/or treatment of diseases such as calcium pathobolism and osteoporosis, the compound of this invention may be administered to mammals in a dose of about 25 to about 400 ng/day, preferably about 50 to 200 ng/day. This dose range, however, is a provisional criterion, and the compound may be administered in doses outside this range by a physician's judgement depending upon the condition, sex, age and weight, for example, of a patient. The administration may be effected orally or parenterally through various routes (e.g., subcutaneous, intramuscular, intravenous, intraperitoneal, and intrarectal).

The compound of this invention may be formulated into a dosage form according to the route of administration. For example, for oral administration, it can be formulated into tablets, capsules, granules, powders, syrups, elixirs, etc. For parenteral administration, it can be formulated into injectable preparations, drops, suppositories, etc. A pharmaceutical composition in such dosage forms may be prepared by mixing an effective amount of the compound of this invention with a pharmaceutically acceptable carrier or diluent (adjuvant) and formulating the mixture into the desired dosage form in a usual manner.

Illustrative of the adjuvant which may be incorporated in solid preparations such as tablets, capsules, granules and powders are binders such as tragacanth gum, acacia, corn starch or gelatin; excipients such as dicalcium phosphate, disintegrants such as corn starch, potato starch or alginic acid; lubricants such as magnesium stearate; sweetening agents such as sucrose, lactose or saccharin; and flavoring agents such as peppermint, oil of wintergreen or cherry. Various other materials may be present as coatings or in order to otherwise modify the physical form of the dosage unit. For example, tablets may be coated with shellac, sugar, or both. The syrup or elixir may contain the active compound, sucrose as a sweetening agent, methyl and propyl parabvens as preservatives, a dye and a cherry or orange flavor.

Sterile compositions for injection can be formulated according to the conventional practice of pharmaceutical preparation by dissolving or suspending the active compound in a vehicle such as water for injection, a natural vegetable oil such as sesame oil, coconut oil, peanut oil or cottonseed oil, or a synthetic fatty vehicle such as ethyl oleate. Buffers, preservatives, antioxidants and the like may be incorporated as required.

What is claimed is:

1. (24ξ)-28,28,28-trifluoro-25-hydroxyvitamin $D_2$.

* * * * *

UNITED STATES PATENT AND TRADEMARK OFFICE
CERTIFICATE OF CORRECTION

PATENT NO. : 5,047,564

DATED : September 10, 1991

INVENTOR(S) : KOBAYASHI et al

It is certified that error appears in the above-identified patent and that said Letters Patent is hereby corrected as shown below:

Column 2, line 23, "trifluoromethyI" should read should read --trifluoromethyl--.

Column 7, line 50, after "A" insert a colon --:--.

Column 10, line 19, delete "13";

line 22, "(8a-8b):" should read --(8a-8d):--; and line 44, "(20 mg)" should read --(120 mg)--.

Column 11, line 21, "25-dio-" should read --25-diol---; and line 33, "55 ng" should read --55 mg--.

Column 12, line 27, "4Hz)," should read --6.4Hz),--;

UNITED STATES PATENT AND TRADEMARK OFFICE
CERTIFICATE OF CORRECTION

PATENT NO. : 5,047,564
DATED : September 10, 1991
INVENTOR(S) : KOBAYASHI et al

Page 2 of 4

It is certified that error appears in the above-identified patent and that said Letters Patent is hereby corrected as shown below:

line 29, "$^{19}$FNMR" should read --$^{19}$F-NMR--;

line 37, "p-toluenesulfonic" should read --p-toluene-sulfonic--;

line 48, after "980" insert a comma --,--;

line 54, delete "9.0)HZ)." and insert --9.0Hz).--; and line 63, after "2.78(1H, m)," insert --3.14(1H, s), 3.64(1H, m), 5.26-5.37(1H, m),--.

Column 14, line 40, delete "of", second instance;

line 55, "3.46(1H," should read --3.46(3H,--; and line 58, "8.78Hz)," should read --8.7Hz),--.

Column 16, line 38, delete "295(M +$^{-OH)}$, 281(M +$^{-CH_2OH}$)." and insert --295(M$^+$ -OH), 281(M$^+$ -CH$_2$OH).--; and

UNITED STATES PATENT AND TRADEMARK OFFICE
CERTIFICATE OF CORRECTION

PATENT NO. : 5,047,564

DATED : September 10, 1991

INVENTOR(S) : KOBAYASHI et al

It is certified that error appears in the above-identified patent and that said Letters Patent is hereby corrected as shown below:

line 42, delete "($^{19}$):" and insert --(19):--.

Column 17, line 8, "($^{19}$)" should read --(19)--;

line 27, "J  ," should read --$J_{gem}$--;

line 32, "F:$^{19.24,}$" should read --F:19.24,--;

line 33, "F:$^{19.01,}$" should read --F:19.01,--; and line 37, "ml" should read --mg--.

Column 18, line 3, "5 37(1H, m)," should read --5.37(1H, m),--;

line 9, "28-trifluoroergosta5," should read --28-trifluoroergosta-5--;

line 21, "(CDC13)" should read --(CDCl$_3$)--;

line 25, "wa/ as" should read --way as--;

line 64, "D$_2$R$_1$" should read --D$_2$ [R$_1$--; and line 68, "D$_2$ R$_1$ = CF ," should read --D$_2$ [R$_1$ = CF$_3$,--.

UNITED STATES PATENT AND TRADEMARK OFFICE
CERTIFICATE OF CORRECTION

PATENT NO. : 5,047,564
DATED : September 10, 1991
INVENTOR(S) : KOBAYASHI et al It is certified that error appears in the above-identified patent and that said Letters Patent is hereby corrected as shown below:

Column 19, line 3, "-25-" should read --1, 25--; and line 24, "($^{1984}$)." should read --(1984).--.

Column 20, line 10, "(MUTO-ID$_{20}$BL)" should read --(MUTO-ID20BL)--.

Signed and Sealed this

Thirteenth Day of April, 1993

*Attest:*

STEPHEN G. KUNIN

*Attesting Officer*   Acting Commissioner of Patents and Trademarks